United States Patent [19]

Igarashi et al.

[11] Patent Number: 5,521,216

[45] Date of Patent: May 28, 1996

[54] CHROMONE DERIVATIVE, AND ALDOSE REDUCTASE INHIBITOR COMPRISING SAID COMPOUND AS ACTIVE INGREDIENT

[75] Inventors: Yasushi Igarashi; Takuji Yamaguchi; Kunio Hosaka, all of Ibaraki, Japan

[73] Assignee: Tsumura & Co., Tokyo, Japan

[21] Appl. No.: 182,028

[22] PCT Filed: May 26, 1993

[86] PCT No.: PCT/JP93/00699

§ 371 Date: May 12, 1994

§ 102(e) Date: May 12, 1994

[87] PCT Pub. No.: WO93/24477

PCT Pub. Date: Dec. 9, 1993

[30] Foreign Application Priority Data

May 27, 1992 [JP] Japan ................... 4-135316

[51] Int. Cl.⁶ .................. A61K 31/35; C07D 311/16
[52] U.S. Cl. ............................. 514/456; 549/400
[58] Field of Search ................ 549/400; 514/456

[56] References Cited

FOREIGN PATENT DOCUMENTS 1-228914  9/1989  Japan .
2-169586  6/1990  Japan .

OTHER PUBLICATIONS

Komiya et al., Journal of the Pharmaceutical Society of Japan, vol. 96, No. 7, Jul. 1976, pp. 841–854.
Komiya et al., Journal of the Pharmaceutical Society of Japan, vol. 96, No. 7, Jul. 1976, pp. 855–862.
Tanimoto, Pharmacia, vol. 24, pp. 459–463, 1988.
Igarashi et al. CA. 117: 233,854f (1992)–Abstract of WO92 09594, Jun. 11, 1992.

*Primary Examiner*—Nicky Chan
*Attorney, Agent, or Firm*—Finnegan, Henderson, Farabow, Garrett & Dunner

[57] ABSTRACT

The present invention relates to a chromone derivative of formula (1):

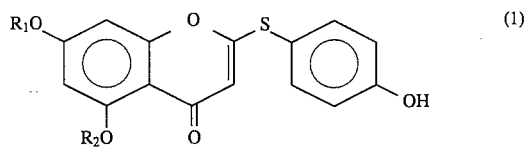

(wherein $R_1$ and $R_2$ are the same or different and independently represent a hydrogen atom or a lower alkyl group) as well as a synthetic intermediate thereof and an aldose reductase inhibitor comprising said derivative as an active ingredient. The chromone derivatives of the present invention can be easily synthesized, and are useful as aldose reductase inhibitor with an excellent inhibitory action on aldose reductase.

10 Claims, No Drawings

CHROMONE DERIVATIVE, AND ALDOSE REDUCTASE INHIBITOR COMPRISING SAID COMPOUND AS ACTIVE INGREDIENT

This application is a 371 of PCT/JP93/00699, filed May 26, 1993.

TECHNICAL FIELD

The present invention relates to chromone derivatives with an inhibitory action on aldose reductase which are effective for the treatment of complications due to diabetes, as well as to synthetic intermediates and utilities of said derivatives.

TECHNICAL BACKGROUND

In recent years, attention is drawn to the accumulation of sorbitol in cells via a polyol pathway, i.e. a metabolic pathway of glucose, as a causative factor of various complications of diabetes such as cataract, retinosis, keratopathy, nephrosis, peripheral nervous system disorder, etc. The polyol pathway, proved to occur widely in various internal organs by immunotissue-chemical means, is a metabolic pathway in which aldoses such as glucose, galactose, etc., are converted through polyols e.g. sorbitol, galactitol, etc., into ketoses such as fructose, etc.

The enzyme catalyzing the conversion of aldoses into polyols in the first step of this pathway is called aldose reductase, and is considered the rate-limiting enzyme in the polyol pathway. It was reported that various complications in patients with diabetes are effectively prevented and cured by inhibiting aldose reductase and lowering sorbitol production and accumulation (Pharmacia, 24: 459 (1988)).

Under the circumstances, the development of pharmaceuticals with an inhibitory action on aldose reductase has been desired.

As pharmaceuticals with an inhibitory action on aldose reductase, Japanese Patent Appln. LOP Publication No. 228,914/89 discloses chromone derivatives Capillarisin (R=H) and 7-methyl Capillarisin (R=CH$_3$) isolated from the herb of Artemisia capillaris thumb, represented by formula:

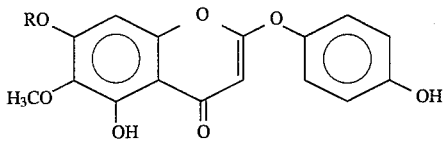

Known compounds with a similar structure to Capillarisin include the chromone derivatives of formula (A):

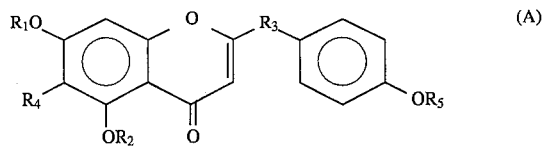

wherein R1, R2, R3, R4 and R5 are set out in Table 1 (for example, Japanese Patent Appln. LOP Publication Nos. 169,586/90, 114,768/79 and 322,066/88 and Journal of the Pharmaceutical Society of Japan, 96: 841 (1976) and 96: 855 (1976)). However, it has not be made evident whether these chromone derivatives have any inhibitory action on aldose reductase.

TABLE 1

| R$_1$ | R$_2$ | R$_3$ | R$_4$ | R$_5$ |
|---|---|---|---|---|
| CH$_3$ | H | O | OCH$_3$ | CH$_3$ |
| CH$_3$ | CH$_3$ | O | OCH$_3$ | CH$_3$ |
| C$_2$H$_5$ | H | O | OCH$_3$ | C$_2$H$_5$ |
| C$_2$H$_5$ | C$_2$H$_5$ | O | OCH$_3$ | C$_2$H$_5$ |
| COCH$_3$ | COCH$_3$ | O | OCH$_3$ | COCH$_3$ |
| H | H | S | OCH$_3$ | H |
| H | CH$_3$ | O | H | H |
| CH$_3$ | CH$_3$ | O | H | CH$_3$ |
| CH$_3$ | H | O | H | H |
| H | H | O | H | H |
| H | H | O | H | CH$_3$ |
| CH$_3$ | H | O | H | CH$_3$ |

DESCRIPTION OF THE INVENTION

The object of the present invention is to provide chromone derivatives which can be easily synthesized without using Capillarisin as a starting material and which exhibits aldose reductase inhibition superior to that of Capillarisin.

The present first invention relates to the chromone derivatives represented by formula (1):

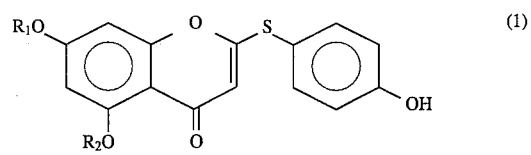

wherein R1 and R2 are the same or different and independently represent a hydrogen atom or a lower alkyl group.

In the above formula (1), the lower alkyl groups represented by R$_1$ or R$_2$ are C$_{1-6}$ alkyl groups, such as methyl, ethyl, propyl, isopropyl, butyl, isobutyl, sec-butyl, tert-butyl, pentyl, isopentyl, 1-ethylpropyl and hexyl groups.

For the chromone derivative (1) of the present invention, at least one of R$_1$ and R$_2$ in the above formula (1) is preferably a branched-chain alkyl group, such as an isopropyl group, represented by formula (3):

wherein R$_7$ and R$_8$ are the same or different and independently represents a methyl or ethyl group.

Examples of the present chromone derivative (1) are 5,7-dihydroxy-2-(4-hydroxyphenylthio)chromone, 5-hydroxy-2-(4-hydroxyphenylthio)-7-methoxychromone, 2-(4-hydroxyphenylthio)-5,7-dimethoxychromone, 5,7-diethoxy-2-(4-hydroxyphenylthio)chromone, 5-hydroxy-2-(4-hydroxyphenylthio)-7-isopropoxychromone, 2-(4-hydroxyphenylthio)-7-isopropoxy-5-methoxychromone, 5-ethoxy-2-(4-hydroxyphenylthio)-7-isopropoxychromone, 2-(4-hydroxyphenylthio)-5,7-diisopropoxychromone, 2-(4-hydroxyphenylthio)-5,7-dipropoxychromone, 5,7-dibutoxy-2-(4-hydroxyphenylthio)chromone, 5,7-di-s-butoxy-2-(4-hydroxyphenylthio)chromone, 7-s-butoxy-2-(4-hydroxyphenylthio)-5-isopropoxychromone, 7-s-butoxy-5-ethoxy-2-(4-hydroxyphenylthio)chromone, 7-s-butoxy-2-(4-hydroxyphenylthio)-5-methoxychromone and 7-(1-ethylpropoxy)-2-(4-hydroxyphenylthio)-5-methoxychromone.

The compound (I) of the present invention can be prepared for example in the following manner.

A commercial phloroacetophenone is alkylated on at least one of hydroxy groups at the 2'-, 4'-, and 6'-positions, followed by reaction with t-butoxy potassium and carbon disulfide, to yield a thion compound. The product is then methylated, thus giving rise to sulfide. It is then oxidized with an oxidizing agent such as peroxy acid, oxone, sodium periodate, etc., to give sulfoxide (referred to hereinafter as "Intermediate (I)") which in turn is substituted by 4-hydroxybenzenethiol in the presence of a base, whereby the present compounds can be obtained.

Examples of alkyl halide include alkyl iodide, such as methyl iodide, ethyl iodide, propyl iodide, isopropyl iodide, butyl iodide, isobutyl iodide, s-butyl iodide, etc., and alkyl bromide, such as methyl bromide, ethyl bromide, etc.

The above alkylation preferably makes use of a base such as potassium carbonate etc. and may be effected at room temperature or at about 50°–60° C. under heating for improvement of reaction efficiency etc., if necessary under reflux etc.

Alternatively, the compound of the present invention can obtained in the following manner.

2'-hydroxy-4',6'-bis(methoxymethoxy)acetophenone is allowed to react with carbon disulfide in the presence of a base such as potassium t-butoxy, lithium di-isopropylamide, potassium hydride, etc., in a solvent such as THF, toluene, benzene, 1,2-dimethoxyethane, N,N-dimethylformamide (DMF), dimethylsulfoxide, diglyme, hexamethylphosphoramide, etc., followed by methylation to give 5,7-bis-(methoxymethoxy)-2-methylthiochromone of formula (2):

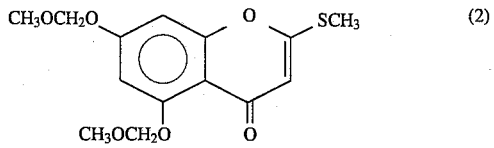

This compound is deprotected by treatment with an acid such as hydrochloric acid, phosphoric acid, sulfuric acid, etc., to give 5,7-dihydroxy-2-methylthiochromone which is then alkylated on hydroxyl group(s) at the 7-position or the 5- and 7-positions as necessary in the chromone skeleton. In the same manner as described above, the alkyl group(s) is oxidized and then replaced by 4-hydroxybenzenthiol, to give the present compound.

The synthetic intermediate of the above formula (2) is a new compound, and it is another object of the invention to provide said new synthetic intermediate.

Purification of the product includes conventional methods e.g. column chromatography on a carrier such as silica gel etc. and recrystallization from methanol, ethanol, chloroform, dimethylsulfoxide, water, etc. Examples of eluting solvent in column chromatography are chloroform, acetone, hexane, dichloromethane, and ethyl acetate.

The chromone derivative (1) of the invention exhibits excellent inhibition on aldose reductase and are effective as medicaments for treatment of various complications due to diabetes, such as cataract, retinosis, keratopathy, nephrosis, peripheral nervous system disorder, etc.

A further object of the present invention is to provide an aldose reductase inhibitor comprising the chromone derivative of the above formula (1) as an active ingredient.

Hereinafter, the inhibitory action of the present compounds on aldose reductase is described with reference to Experimental Examples.

EXPERIMENTAL EXAMPLE 1

<Aldose reductase activity measurement (in vitro)>

6 week-old Wistar male rats were sacrificed under ether anesthesia and immediately the crystalline lenses were scissored and stored at −20° C.

The crystalline lenses were homogenized in 135 mM sodium-potassium-phosphate buffer, pH 7.0, and centrifuged for 30 min. at 30,000 rpm. The supernatant was used as an aldose-reductase solution. All the above procedures were carried out at 4° C. and the enzyme solution was stored at −20° C.

Aldose reductase activity was determined according to the method as described by Dufrane et al. (Biochemical Medicine, 32, 99–105 (1984)), as follows.

100 µl of the above enzyme solution and 100 µl of a sample solution prepared by dissolving a compound obtained in the following examples to a final concentration of from $1.0 \times 10^{-5}$ to $4.0 \times 10^{-7}$M in dimethylsulfoxide (DMSO) were added to 800 µl of 135 mM sodium-potassium-phosphate buffer, pH 7.0, containing 100 mM lithium sulfate, 0.03 mM NADPH (reduced nicotinamide adenine dinucleotide phosphate), and 20 mM glucose as a substrate. The sample was allowed to react for 30 min. at 30° C. Then the reaction was stopped by addition of 0.3 ml of 0.5N hydrochloric acid. By adding 1 ml of 6N sodium hydroxide containing 10 mM imidazole, the NADP (oxidized nicotinamide adenine dinucleotide phosphate) formed in the above reaction was converted into a fluorescent substance, and 30 min. thereafter, the sample was measured for fluorescence intensity at the fluorescence wavelength of 460 nm (excitation wavelength: 360 nm) using fluorescence photometer F-4000 (manufactured by Hitachi, Ltd.) at room temperature. A sample containing DMSO in place of the present compound was used as a control group, and its fluorescence intensity was determined in the same manner as described above.

Aldose reductase is an enzyme that converts DL-glyceraldehyde or glucose into polyol in the presence of NADH as a coenzyme, and as the reaction proceeds, NADPH is converted into NADP. Hence, the less formation of NADP indicates the higher inhibition of aldose reductase.

EXPERIMENTAL EXAMPLE 2

<Aldose reductase activity measurement (in vivo)>

A solution of streptozotocin (STZ) in 10 mM citrate buffer (pH 4.5) was administered intravenously to the tails of 6 week-old Wistar male rats in a dosage of 65 mg/kg. 48 hours thereafter, blood was collected from the carotid arteries of the rats. Rats with a blood sugar level of higher than 200 mg/dl were classified as diabetic rats, among which rats with a persistent high level of blood sugar were employed in the experiment. The blood sugar level was determined by the glucose oxidase method.

A compound obtained in the following examples was suspended in purified water or 0.5% carboxy sodium cellulose solution, and 2 weeks after the administration of STZ, the suspension was orally administered into a rat in a dosage of 30 mg/kg for 2 weeks.

After 2-week administration, the sciatic nerves were removed from the rat under ether anesthesia, then weighed, and stored at −20° C.

The content of sorbitol in the sciatic nerves was determined as follows.

The sciatic nerves were extracted at 100° C. for 20 min. with 1 ml purified water containing 10 µg/ml arabinitol, and then 0.2 ml of 0.2M barium hydroxide and 0.2 ml of 0.19M zinc sulfate were added thereto. The sample was centrifuged (3000 rpm, 30 min.) and the supernatant was evaporated to dryness. The residue thus obtained was trimethysilylated and was then analyzed by gas chromatography.

Sorbitol is an intermediate which occurs upon the conversion of glucose into fructose by aldose reductase and is accumulated together with fructose in the crystalline lenses and sciatic nerves particularly under a high level of blood sugar. Therefore, the less formation of sorbitol indicates the higher inhibition of aldose reductase.

Table 2 shows inhibition rate (%) by 10 μM of the present compounds, 50%-inhibition concentration [$IC_{50}$ (M)], and repression rate (%) at 30 mg/kg.

TABLE 2

|  | 50% inhibition concentration [$IC_{50}$ (M)] | Inhibition (%) | Repression (%) |
|---|---|---|---|
| Compound in Example 1 | $1.8 \times 10^{-8}$ | 97.7 |  |
| Compound in Example 2 | $1.0 \times 10^{-7}$ | 88.7 |  |
| Compound in Example 3 | $1.0 \times 10^{-7}$ | 84.0 |  |
| Compound in Example 4 | $3.2 \times 10^{-7}$ |  |  |
| Compound in Example 5 | $2.3 \times 10^{-7}$ |  |  |
| Compound in Example 6 | $8.0 \times 10^{-8}$ |  |  |
| Compound of Formula (B) | $1.8 \times 10^{-7}$ | 94.5 |  |
| Capillarisin | $1.6 \times 10^{-6}$ | 81.0 | 18.9 (100 mg/kg) |

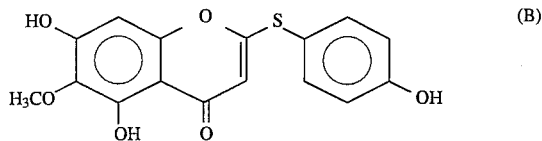

(B)

ICR strain mice were examined for the acute toxicity of the present compounds by oral administration. As a result, every mouse survived at a dosage of 1 g/kg, indicating the very low toxicity and high safety of the present compounds.

The dosage and pharmaceutical manufacturing of the present compounds are described below.

The compounds of the present invention can be administered into animal and human singly or in combination with a conventional pharmaceutical carrier. The form of the present compounds administered can be suitably selected as necessary, including, but not particularly limited to, tables, capsules, granules, fine granules, powder, etc., for oral administration and injection liquid, suppositories, etc., for parenteral administration.

To demonstrate the desired effect in oral administration, the present compound is administered into an adult preferably at a dosage of 30 mg to 2 g per day at suitable intervals, depending on the age, weight and disease severeness of the patient.

A preparation for oral administration is manufactured in a usual manner using starch, milk sugar, white sugar, mannitol, carboxymethylcellulose, corn starch, inorganic salts, etc.

This type of pharmaceutical preparation can make use of binders, disintegrants, surface active agents, lubricants, fluidity promoters, corrigents, colorants, perfumes, etc., in addition to the vehicles enumerated above. As specific examples, binders are starch, dextrin, powder of gum arabic, gelatin, hydroxypropyl starch, methyl cellulose, carboxymethylcellulose sodium, hydroxypropylcellulose, crystalline cellulose, ethyl cellulose, polyvinylpyrrolidone, and macrogol; disintegrants are starch, hydroxypropyl starch, carboxymethylcellulose sodium, carboxymethylcellulose calcium, carboxymethyl cellulose, low-substituted hydroxypropyl cellulose; surface active agents are sodium lauryl sulfate, soybean lecithin, sucrose fatty acid ester, Polysolvate 80; lubricants are talc, waxes, hydrogenated vegetable oils, sucrose fatty acid ester, magnesium stearate, calcium stearate, aluminum stearate, polyethylene glycol; and fluidity promoters are light silicic anhydride, dried gel of aluminum hydroxide, synthetic aluminum silicate, magnesium silicate.

The present compounds can be administered in the form of suspension, emulsion, syrup and elixir, each form of which may contains correctives and coloring agents.

To demonstrate the desired effect in parenteral administration, the present compound is administered into an adult at intravenously, subcutaneously, intramuscularly, or by intravenous drip injection preferably at a dosage of 0.1 to 600 mg per day at suitable intervals, depending on the age, weight and disease severeness of the patient.

A preparation for parenteral administration is manufactured in a usual manner, which may make use of such diluents as distilled water for injection, physiological saline, an aqueous glucose solution, vegetable oil for injection, sesame oil, peanut oil, soybean oil, corn oil, polypropylene glycol, polyethylene glycol, etc. Additives such as disinfectants, antiseptics and stabilizers may be incorporated as necessary. For keeping stability, such a parenteral preparation can be lyophilized in vials etc. by conventional techniques in order to reconstitute a liquid preparation just before use. Furthermore, additives such as isotonic agents, stabilizers, disinfectants and soothing agents may also be incorporated as necessary.

Other examples of the parenteral preparation are surgical liquid drugs and ointments as well as suppositories for administration into the rectum, and these are manufactured in accordance with a usual manner.

THE BEST MODE FOR CARRYING OUT THE INVENTION

The present invention is explained in detail with reference to the following examples, which however are not intend to limit the scope of the invention.

SYNTHETIC EXAMPLE 1

336.0 g of potassium t-butoxy was suspended in 2 liters of toluene. Under cooling on ice, 2 liters of 196.0 g of 2'-hyroxy-4',6'-dimethoxyacetophenone and 72.0 ml carbon disulfide in toluene were added dropwise to said suspension. The mixture was stirred for 20 hours at room temperature, and 7 liters of water was added for extraction of a toluene layer. This toluene solution was adjusted to pH 4–5 by addition of 800 ml of 10% sulfuric acid (aq.) and was then stirred for 5 hours at room temperature. The solution was allowed to stand overnight. The resulting yellow crystals were collected by filtration under reduced pressure, sufficiently washed with water and dried at 50° C. for 3 days under reduced pressure, thus giving rise to 160.0 g crude 4-hydroxy-5,7-dimethoxychromene-2-thion.

160.0 g of the product 4-hydroxy-5,7-dimethoxychromene-2-thion and 110.4 g of potassium carbonate were suspended in 4.8 liters of water. 125.0 ml methyl iodide was added to the suspension at room temperature, followed by 2.5-hour stirring. The resulting crystals were collected by filtration under reduced pressure, sufficiently washed with water, and dried at 60° C. under reduced pressure, to give 146.8 g of crude 5,7-dimethoxy-2-methylthiochromone. 146.8 g of the product 5,7-dimethoxy-2-methylthiochromone was suspended in 3 liters of methanol. Under cooling on ice, 1.5 liters of 252.2 g oxone in water was added thereto, followed by 3-hour stirring at room temperature. 4 liters of water were added to the reaction solution which was then extracted twice with dichloromethane (4 liters and 2 liters, respectively), and the organic layer was washed with saturated NaCl water and dried over sodium sulfate anhydride. The solvent was distilled off under reduced pressure. The crude product was subjected to recrystallization from 8 liters of methanol, to give 91.5 g of 5,7-dimethoxy-2-methylsulfinylchromone (Intermediate (1)).

EXAMPLE 1

A mixture solution of 8.37 g of phloroacetophenone, 25.0 g of isopropyl iodide, 20.62 g of potassium carbonate and 120 ml of acetone was stirred for 2 days under reflux in a bath at 60° C. The reaction solution was neutralized with dilute hydrochloric acid and then extracted twice with ethyl acetate. The organic layer was washed with saturated NaCl water and was then dried over sodium sulfate anhydride. The solvent was distilled off under reduced pressure. The resulting crude crystals, 12.46 g, were purified by flash column chromatography (hexane: ethyl acetate=40 : 1), thus giving 9.46 g diisopropyl body.

Under cooling on ice, 399 mg of potassium t-butoxy was suspended in 10 ml THF, followed by addition of 3 ml THF solution of 225 mg of the diisopropyl body and 3 ml THF solution of 135 mg carbon disulfide. After stirred overnight at room temperature, methyl iodide was added to the reaction solution which was then stirred for additional 1 hour. After water was added thereto, the reaction solution was extracted twice with ethyl acetate, and the organic layer was washed with saturated NaCl water and was then dried over sodium sulfate anhydride. The solvent was distilled off under reduced pressure and the oil residue, 345 mg, was purified by flash column chromatography (chloroform: acetone=10 : 1), to give sulfide.

A mixture of 136 mg of the sulfide, 271 mg of oxone, 3 ml methanol and 3 ml water was stirred for 2 hours at room temperature. Following addition of water, the reaction solution was extracted twice with chloroform, and the organic layer was washed with saturated NaCl water and dried over sodium sulfate anhydride. The solvent was distilled off under reduced pressure, and 80 mg of the resulting crude crystals was purified by flash column chromatography (chloroform: acetone=30 :1), to give 31 mg sulfoxide.

A mixture of 29 mg of the sulfoxide, 23 mg of 4-hydroxybenzenethiol and 25 mg of potassium carbonate in 3 ml acetone was stirred for 20 hours at room temperature. After addition of water, the reaction solution was made weakly acidic by addition of dilute hydrochloric acid, and the resulting precipitates were recovered by filtration, then washed with water and dried. The resulting crude crystals, 29 mg, were recrystallized from 2 ml methanol, to give 17 mg of 2-(4-hydroxyphenylthio)-5,7-di-isopropoxychromone with the following physicochemical properties:

Melting point: 234°~236° C.

Infrared absorption spectrum (IR) ($v_{max}$ cm$^{-1}$, KBr): 2980, 1612, 1578, 1498, 1452, 1426, 1380, 1322, 1286, 1112

Proton nuclear magnetic resonance spectrum ($^1$H-NMR) (δ ppm, in CDCl$_3$):

7.47 (2H, d, J=8.3 Hz), 6.92 (2H, d, J=8.3 Hz), 6.56 (1H, d, J=2.4 Hz), 6.41 (1H, d, J=2.4 Hz), 5.32 (1H, s), 4.76 (1H, h, J=6.1 Hz), 4.59 (1H, h, J=6.1 Hz), 1.29 (6H, d, J=6.1 Hz), 1.25 (3H, d, J=6.1 Hz)

Mass spectrum (MS) (EI-MS) m/z (%):

386, 371,344, 328, 302, 286, 150

High-resolution mass spectrum (HRMS): $C_{21}H_{22}O_5S$
Calculated ; 386.11876
Found ; 386.11596

EXAMPLE 2

3.89 g of intermediate (1) obtained in Synthesis Example 1, 2.43 g of 4-hydroxybenzenethiol and 1.40 g of sodium hydroxide were introduced in a reaction vessel. The air in the vessel was replaced by nitrogen and 78 ml absolute dimethyl sulfoxide was introduced thereinto. The mixture was stirred overnight at room temperature. The reaction solution was then poured into ice-cold 1N hydrochloric acid. The insolubles thus precipitated were collected by filtration and sufficiently washed with water, to give a white solid. This product was recrystallized from methanol-chloroform-n-hexane, thus giving rise to 2-(4-hydroxyphenylthio)-5,7-dimethoxychromone, 3.18 g, in the form of colorless fine needle crystals.

Melting point: 272°~275° C.

IR ($v_{max}$ cm$^{-1}$, KBr):

3208, 1626, 1578, 1496, 1458, 1330, 1272, 1204, 1164, 1124,.1106, 1060, 920, 834, 692, 670, 598, 528

$^1$H-NMR (δ ppm, in DMSO-d$_6$):

3.79 (3H, s), 3.86 (3H, s), 5.36 (1H, s), 6.49 (1H, d, J=2.4 Hz), 6.61 (1H, d, J=2.4 Hz), 6.93 (2H, d, J=8.8 Hz), 7.50 (2H, d, J=8.8 Hz), 10.22 ( 1H, s )

MS (EI-MS) m/z (%) :

330 (100,M$^+$), 313 (6), 301 (26), 284 (36), 181 (9), 151 (32)

Elementary analysis: $C_{17}H_{14}O_5S$
Calculated; C : 61.81, H : 4.27
Found; C : 61.49, H: 4.24

EXAMPLE 3

2.22 g of 2-(4-hydroxyphenylthio)-5,7-dimethoxychromone obtained in Example 2 was introduced into a reaction vessel and the air in the vessel was replaced by nitrogen. 25 ml absolute methylene chloride was added and the sample was suspended. 25 ml of 0.8M boron tribromide in methylene chloride was added at −40° C. to the sample suspension, followed by stirring at −40° C. for 10 min. and subsequent stirring at room temperature for 1 hour. The reaction solution was poured into 300 ml ice water, and the resulting insolubles were collected by filtration and washed sufficiently with water, thus giving a yellow solid. This product was then recrystallized from acetone-n-hexane, to give rise to 1.57 g of colorless needle crystals of 5-hydroxy-2-(4-hydroxyphenylthio)-7-methoxychromone.

IR ($v_{max}$ cm$^{-1}$, KBr):

3164, 1660, 1590, 1494, 1436, 1336, 1286, 1198, 1166, 1130, 1110, 1040, 916, 860, 832, 800, 766, 686, 538, 524

$^1$H-NMR (6 ppm, in DMSO-d$_6$):

3.83 (3H, s), 5.51 (1H, s), 6.38 (1H,d,J=2.4 Hz), 6.59 (1H, d, J=2.4 Hz), 6.96 (2H, d, J=8.8 Hz), 7.52 (2H, d, J=8.8 Hz), 10.29 (1H, s), 12.61 (1H, s)

MS (EI-MS) m/z (%):
316 (100, M$^+$), 287 (13), 167 (53), 150 (30), 138 (10), 121 (12), 95 (10)
Elementary analysis: $C_{16}H_{12}O_5S$
Calculated; C : 60.75, H : 3.82
Found; C : 60.77, H : 3.84

EXAMPLE 4

(1) Under cooling on ice, potassium hydride (0.5 ml of 35% mineral oil) was suspended in 2 ml THF. 2 ml of 126 mg of 2'-hydroxy-4',6'-bis(methoxymethoxy)acetophenone (0.492 mmol) and 130 mg of 18-crown-6 (0.492 mmol) in THF was added dropwise to the above suspension, and the mixture was stirred for 1 hour. After addition of 0.89 ml of carbon disulfide (14.76 mmol), the solution was stirred for 20 hours at room temperature. Then, 0.5 ml of methyl iodide was added thereto, and the solution was stirred for 30 min. After water was slowly added thereto, the reaction solution was extracted twice with ether, and the organic layer was washed with saturated NaCl water and then dried over sodium sulfate anhydride. The solvent was distilled off and the resulting crude product was washed with hexane, to give 133.5 mg of 5,7-bis(methoxymethoxy)-2-methylthiochromone (87% yield).

Melting point: 109°~110° C.
IR ($v_{max}$ cm$^{-1}$, KBr):
1640, 1620, 1588, 1316, 1152, 1126, 1092, 1074, 1036, 904
$^1$H-NMR (δ ppm, in CDCl$_3$):
6.37 (d, 2.5 Hz, 1H), 6.71 (d, 2.5 Hz, 1H), 6.04 (s, 1H), 5.31 (s, 2H), 5.22 (s, 2H), 3.55 (s, 3H), 3.50 (s, 3H), 2.49 (s, 3H)
MS (FAB) : 313(MH$^+$)
HRMS : $C_{14}H_{17}O_6S$
Calculated; 313.07459
Found; 313.07433

(2) Under cooling on ice, 70 ml of hydrochloric acid/methanol was added to 70 ml of 9.47 g of 5,7-bis-(methoxymethoxy)-2-methylthiochromone (30.35 mmol) in THF, and the mixture was stirred overnight at room temperature. After addition of water, the reaction solution was extracted twice with ethyl acetate, and the organic layer was washed with saturated NaCl water and dried over sodium sulfate anhydride. The solvent was distilled off under reduced pressure, to give 6.88 g of 5,7-dihydroxy-2-methylthiochromone. This product was subjected without purification to the following reaction.

Melting point: 244°~246° C.
IR ($v_{max\,cm}$$^{-1}$, KBr):
1650, 1610, 1582, 1564, 1498, 1354, 1346, 1164
$^1$H-NMR (δ ppm, in acetone-d$_6$):
12.82 (s, 1H), 9.70 (brs, 1H), 6.37 (d, 2.0 Hz, 1H), 6.23 (d, 2.0 Hz, 1H), 2.64 (s, 3H)
MS (FAB) : 225 (MH$^+$)
HRMS : $C_{10}H_9O_4S$
Calculated; 225.02216
Found; 225.02406

(3) 1 ml aqueous solution of 82 mg oxone (0.134 mmol) was added dropwise to 1 ml of 30 mg of 5,7-dihydroxy-2-methylthiochromone (0.134 mmol) in methanol at room temperature, and the mixture was stirred for 1 hour. After addition of water, the reaction solution was extracted twice with ethyl acetate, and the organic layer was washed with saturated NaCl water and dried over sodium sulfate anhydride. The solvent was distilled off under reduced pressure, to give 32 mg of 5,7-dihydroxy-2-methylsulfinylchromone (containing a little sulfone). This product was subjected without purification to the following reaction.

$^1$H-NMR (δ ppm, in acetone-d$_6$):
12.46 (s, 1H), 6.64 (s, 1H), 6.49 (d, 2.4 Hz, 1H), 6.32 (d, 2.4 Hz, 1H), 3.03 (s, 3H)
MS (FAB): 241 (MH$^+$)
HRMS : $C_{10}H_9O_5S$
Calculated; 241.01856
Found; 241.01707

(4) A mixture of 32 mg of 5,7-dihydroxy-2-methylsulfinylchromone (0.134 mmol), 20 mg of 4-hydroxybenzenethiol (0.161 mmol), 41 mg of potassium carbonate (0.295 mmol) and 2 ml acetone was stirred overnight at room temperature. The reaction solution was neutralized with dilute hydrochloric acid and then extracted twice with ethyl acetate. The organic layer was washed with saturated NaCl water and dried over sodium sulfate anhydride. The solvent was distilled off under reduced pressure, and the crude product was subjected to recrystallization from acetone-hexane, to give 14.6 mg of 5,7-dihydroxy-2-(4-hydroxyphenylthio)chromone (36% yield).

Melting point: 249°–251° C.
IR ($v_{max}$ cm$^{-1}$, KBr):
3400, 1702, 1642, 1604, 1582, 1574, 1500, 1348, 1334, 1164, 830
$^1$H-NMR (6 ppm, in acetone-d$_6$) :
12.72 (s, 1H), 7.56 (d, 8.8 Hz, 2H), 7.05 (d, 8.8 Hz, 2H), 6.33 (d, 2.0 Hz, 1H), 6.23 (d, 2.0 Hz, 1H), 5.54 (s, 1H)
MS (EI) : 302 (M$^+$), 153, 150
HRMS : $C_{15}H_{10}O_5S$
Calculated; 302.02490
Found; 302.02526

EXAMPLE 5

(1) 6.88 g of 5,7-dihydroxy-2-methylthiochromone (30.35 mmol), 12.56 g of potassium carbonate (91.05 mmol), 6.07 ml of isopropyl iodide (60.70 mmol) and 150 ml DMF were stirred at 60° C. for 30 minutes. After addition of water, the reaction solution was extracted twice with ethyl acetate, and the organic layer was washed with saturated NaCl water and was then dried over sodium sulfate anhydride. The solvent was distilled off under reduced pressure, and the crude product was purified by flash column chromatography (hexane : ethyl acetate=4 : 1), to give 6.71 g of 5-hydroxy-7-isopropoxy-2-methylthiochromone (83% yield).

Melting point: 119°~120° C.
IR ($v_{max}$ cm$^{-1}$, KBr):
1664, 1592, 1498, 1484, 1430, 1342, 1322, 1164, 1132, 1110
$^1$H-NMR (δ ppm, in CDCl$_3$) :
12.59 (s, 1H), 6.31 (s, 2H), 6.03 (s, 1H), 4.59 (m, 1H), 2.52 (s, 3H), 1.37 (d, 5.9 Hz, 6H)
MS (FAB) : 267 (MH$^+$), 225
HRMS : $C_{13}H_{15}O_4S$
Calculated; 267.06911
Found; 267.06964

(2) Under cooling on ice, 50 ml of 5.11 g perbenzoic acid (29.51 mmol) in dichloromethane was added dropwise to 150 ml of 6.54 g of 5-hydroxy-7-isopropoxy-2-methylthiochromone (24.59 mmol) in dichloromethane, and the mixture was then stirred for 1 hour. After addition of sodium bicarbonate, the reaction solution was extracted twice with chloroform, and the organic layer was washed with saturated NaCl water and dried over sodium sulfate anhydride. The solvent was distilled off under reduced pressure, whereby 7.01 g of 5-hydroxy-7-isopropoxy-2-methylsulfinylchromone was obtained. This product was subjected without purification to the following reaction.

IR ($\nu_{max}$ Cm$^{-1}$, KBr):
1664, 1608, 1068

$^1$H-NMR ($\delta$ ppm, in CDCl$_3$):
12.27 (s, 1H), 6.81 (s, 1H), 6.37 (s, 2H), 4.62 (m, 1H), 2.96 (s, 3H), 1.38 (d, 6.4 Hz, 6H)

(3) A mixture of 7.01 g of 5-hydroxy-7-isopropoxy-2-methylsulfinylchromone (24.59 mmol), 3.72 g of 4-hydroxybenzenethiol (29.51 mmol), 4.07 g of potassium carbonate (29.51 mmol) and 170 ml acetone was stirred for 1 hour at room temperature. The reaction solution was neutralized with dilute hydrochloric acid and was then extracted twice with chloroform, and the organic layer was washed with saturated NaCl water and then dried over sodium sulfate anhydride. The solvent was distilled off under reduced pressure, and the crude product was subjected to recrystallization from ethanol-methanol, to give 6.64 g of 5-hydroxy-2-(4-hydroxyphenylthio)-7-isopropoxychromone (78% yield).

Melting point: 205°~207° C.
IR ($\nu_{max}$ cm$^{-1}$, KBr):
3300, 1656, 1594, 1496, 1322

$^1$H-NMR ($\delta$ ppm, in CDCl$_3$):
12.26 (s, 1H), 7.97 (brs, 1H), 7.41 (d, 8.8 Hz, 2H), 6.87 (d, 8.8 Hz, 2H), 6.36 (d, 2.4 Hz, 1H), 6.32 (d, 2.4 Hz, 1H), 5.59 (s, 1H), 4.61 (m, 1H), 1.37 (d, 5.9 Hz, 6H)
MS (E) : 344 (M$^+$), 302
HRMS : C$_{18}$H$_{16}$O$_5$S
Calculated; 344.07185
Found; 344.07170

EXAMPLE 6

(1) 354 mg of 5,7-dihydroxy-2-methylthiochromone (1.58 mmol), 1.09 g of potassium carbonate (7.90 mmol), 0.79 ml isopropyl iodide (7.90 mmol) and 20 ml acetone were refluxed overnight. After addition of 2.95 ml methyl iodide (47.4 mmol), the mixture was further refluxed overnight. Following addition of water, the reaction solution was extracted twice with ethyl acetate, and the organic layer was washed with saturated NaCl water and dried over sodium sulfate anhydride. The solvent was distilled off under reduced pressure, and the crude product was purified by flash column chromatography (hexane: ethyl acetate =1 : 3→1:6), to give 228 mg of 7-isopropoxy-5-methoxy-2-methylthiochromone (52% yield).

Melting point: 113°–114° C.
IR ($\nu_{max}$ cm$^{-1}$, KBr):
1640, 1586, 1308, 1124

$^1$H-NMR ($\delta$ ppm, in CDCl$_3$):
6.39 (d, 2.2 Hz, 1H), 6.32 (d, 2.2 Hz, 1H), 6.04 (s, 1H), 4.61 (m, 1H), 3.92 (s, 3H), 2.48 (s, 3H), 1.39 (d, 6.1 Hz, 6H)
MS (FAB) : 281 (MH$^+$), 239
HRMS : C$_{14}$H$_{17}$O$_4$S
Calculated; 281.08476
Found; 281.08588

(2) 2 ml aqueous solution of 347 mg oxone (0.564 mmol) was added dropwise to 4 ml of 158 mg of 7-isopropoxy-5-methoxy-2-methylthiochromone (0.564 mmol) in methanol, and the mixture was stirred for 30 min. After addition of water, the reaction solution was extracted twice with ethyl acetate, and the organic layer washed with saturated NaCl water and dried over sodium sulfate anhydride. The solvent was then distilled off under reduced pressure, thus giving 147 mg of 7-isopropoxy-5-methoxy-2-methylsulfinylchromone (containing a little sulfone). This product was subjected without purification to the following reaction.

$^1$H-NMR ($\delta$ ppm, in CDCl$_3$):
6.73 (s, 1H), 6.45 (d, 2.2 Hz, 1H), 6.38 (d,2.2 Hz, 1H), 4.63 ( m, 1H ), 3.94 ( s, 3H ), 2.95 ( s, 3H ), 1.40 ( d, 6.1 Hz, 6H)

(3) A mixture of 146 mg of 7-isopropoxy-5-methoxy-2-methylsulfinylchromone (0.493 mmol ) , 93 mg of 4-hydroxybenzenethiol(0.740 mmol), 102 mg of potassium carbonate (0.740 mmol) and 6 ml acetone was stirred for 2 hours at room temperature. The reaction solution was neutralized with dilute hydrochloric acid and extracted twice with ethyl acetate, and the organic layer was washed with saturated NaCl water and was then dried over sodium sulfate anhydride. The solvent was distilled off under reduced pressure, and the crude product was subjected to recrystallization from acetone-methanol, to give 102 mg of 2-(4-hydroxyphenylthio)-7-isopropoxy-5-methoxychromone (57% yield).

Melting point: 263°–265° C.
IR ($\nu_{max}$ cm$^{-1}$, KBr):
3200, 1626, 1598, 1582, 1320, 1126

$^1$H-NMR ($\delta$ ppm, in DMSO-d$_6$):
7.48 ( d, 8.5 Hz, 2H ), 6.93 ( d, 8.5 Hz, 2H ), 6.60 ( d, 2.0 Hz, 1H ), 6.42 (d, 2.0 Hz, 1H), 5.32 (s, 1H), 4.78 (m, 1H), 3.78 (s, 3H), 1.30 (d, 6.1 Hz, 6H)
MS (FAB) : 359 (MH$^+$), 317
HRMS : C$_{19}$H$_{19}$O$_5$S
Calculated; 359.09532
Found; 359.09547

EXAMPLE 7

The following compounds were synthesized in the same manner as in Example 6.

(1)  5-ethoxy-2-(4-hydroxyphenylthio)-7-isopropoxychromone (2)  7-s-butoxy-2-(4-hydroxyphenylthio)-5-isopropoxychromone (3)  7-s-butoxy-5-ethoxy-2-(4-hydroxyphenylthio)chromone (4)  7-s-butoxy-2-(4-hydroxyphenylthio)-5-methoxychromone (5) 7-(1-ethylpropoxy)-2-(4-hydroxyphenylthio)-5-methoxychromone

EXAMPLE 8

| | |
|---|---:|
| (1) Corn starch | 44 g |
| (2) Crystalline cellulose | 40 g |
| (3) Carboxylmethyl cellulose calciu | 5 g |
| (4) Light silicic anhydride | 0.5 g |
| (5) Magnesium stearate | 0.5 g |
| (6) Compound obtained in Example 1 | 10 g |
| Total | 100 g |

According to the above formulation, ingredients (1)–(6) were uniformly mixed and compression-molded into tablets (200 mg per tablet) using a tableting machine.

One tablet thus prepared contains 20 mg of the compound obtained in Example 1. 10–25 tablets are orally administered per day into an adult at suitable intervals.

EXAMPLE 9

| (1) Crystalline cellulose | 84.5 g |
| --- | --- |
| (2) Magnesium stearate | 0.5 g |
| (3) Carboxylmethyl cellulose calcium | 5 g |
| (4) Compound obtained in Example 2 | 10 g |
| Total | 100 g |

According to the above formulation, ingredients (1), (4) and a part of (2) were uniformly mixed, then compression-molded and ground. Subsequently, ingredient (3) and the reminder of (2) were added and mixed. The mixture was compression-molded into tablets (200 mg per tablet) using a tableting machine.

One tablet thus prepared contains 20 mg of the compound obtained in Example 2. 10–25 tablets are orally administered per day into an adult at suitable intervals.

EXAMPLE 10

| (1) Crystalline cellulose | 49.5 g |
| --- | --- |
| (2) 10% hydroxypropyl cellulose in ethanol | 35 g |
| (3) Carboxylmethyl cellulose calcium | 5 g |
| (4) Magnesium stearate | 0.5 g |
| (5) Compound obtained in Example 3 | 10 g |
| Total | 100 g |

According to the above formulation, ingredients (1), (2), and (5) were uniformly mixed, then kneaded according to a usual manner, and formed into granules by an extrusion granulating machine. The granules were then dried and ground, followed by being mixed with ingredients (3) and (4). The composition thus prepared was compression-molded into tablets (200 mg per tablet) using a tableting machine.

One tablet thus prepared contains 20 mg of the compound obtained in Example 3. 10–25 tablets are orally administered per day into an adult at suitable intervals.

EXAMPLE 11

| (1) Corn starch | 34.5 g |
| --- | --- |
| (2) Magnesium stearate | 50 g |
| (3) Carboxylmethyl cellulose calcium | 5 g |
| (4) Light silicic anhydride | 0.5 g |
| (5) Compound obtained in Example 4 | 10 g |
| Total | 100 g |

According to the above formulation, ingredients (1) to (5) were uniformly mixed, then compression-molded using a compression molding machine, and crushed using a crusher, followed by being screened so that granules were obtained.

1 g of the granules thus prepared contains 100 mg of the compound obtained in Example 4. 2–5 g granules are orally administered per day into an adult at suitable intervals.

EXAMPLE 12

| (1) Crystalline cellulose | 55 g |
| --- | --- |
| (2) 10% hydroxypropyl cellulose in ethanol | 35 g |
| (3) Compound obtained in Example 5 | 10 g |
| Total | 100 g |

According to the above formulation, ingredients (1) to (3) were uniformly mixed, then kneaded, and formed into granules by an extrusion granulating machine. The granules were then dried and ground, followed by being screened, thereby giving granules.

1 g of the granules thus prepared contains 100 mg of the compound obtained in Example 5. 2–5 g granules are orally administered per day into an adult at suitable intervals.

EXAMPLE 13

| (1) Corn starch | 89.5 g |
| --- | --- |
| (2) Light silicic anhydride | 0.5 g |
| (3) Compound obtained in Example 6 | 10 g |
| Total | 100 g |

According to the above formulation, compounds (1)–(3) were uniformly mixed, and 200 mg of the mixture was introduced into No. 2 Type capsule.

1 capsule thus prepared contains 20 mg of the compound obtained in Example 6. 10–25 capsules are orally administered per day into an adult at suitable intervals.

EXAMPLE 14

| (1) Soybean oil | 5 g |
| --- | --- |
| (2) Distilled water for injection | 89.5 g |
| (3) Soybean phospholipids | 2.5 g |
| (4) Glycerin | 2 g |
| (5) Compound obtained in Example 1 | 1 g |
| Total | 100 g |

According to the above formulation, ingredient (5) was dissolved in ingredients (1) and (3). A solution of ingredients (2) and (4) was added to the mixture, to give an injection emulsion.

APPLICABILITY TO INDUSTRY

The present invention enables whole synthesis of chromone derivatives having an inhibitory action on aldose reductase and being superior to that of naturally occurring Capillarisin, without using Capillarisin as a starting material. The chromone derivatives of the present invention are useful for the treatment of various complications of diabetes, such as cataract, retinosis, keratopathy, nephrosis, peripheral nervous system disorder, etc.

What is claimed is:

1. A chromone derivative represented by formula (1):

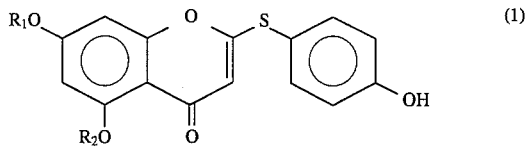

wherein $R_1$ and $R_2$ are the same or different and independently represent a hydrogen atom or a lower alkyl group.

2. The compound according to claim 1, wherein in the above formula (1) at least one of $R_1$ and $R_2$ is a branched-chain alkyl group represented by formula (3):

wherein $R_7$ and $R_8$ are the same or different and independently represent methyl or ethyl group.

3. The compound according to claim 1, wherein in the above formula (1) at least one of $R_1$ and $R_2$ is an isopropyl group.

4. The compound according to claim 1, which is 5,7-dihydroxy-2-(4-hydroxyphenylthio)chromone, 5-hydroxy-2-(4-hydroxyphenylthio)-7-methoxychromone, 2-(4-hydroxyphenylthio)-5,7-dimethoxychromone, 5,7-diethoxy-2-(4-hydroxyphenylthio)chromone, 5-hydroxy-2-(4-hydroxyphenylthio)-7-isopropoxychromone, 2-(4-hydroxyphenylthio)-7-isopropoxy-5-methoxychromone, 5-ethoxy-2-(4-hydroxyphenylthio)-7-isopropoxychromone, 2-(4-hydroxyphenylthio)-5,7-diisopropoxychromone, 2-(4-hydroxyphenylthio)-5,7-dipropoxychromone, 5,7-dibutoxy-2-(4-hydroxyphenylthio)chromone, 5,7-di-s-butoxy-2-(4-hydroxyphenylthio)chromone, 7-s-butoxy-2-(4-hydroxyphenylthio)-5-isopropoxychromone, 7-s-butoxy-5-ethoxy-2-(4-hydroxyphenylthio)chromone, 7-s-butoxy-2-(4-hydroxyphenylthio)-5-methoxychromone or 7-(1-ethylpropoxy)-2-(4-hydroxyphenylthio)-5-methoxychromone.

5. The compound according to claim 1, which is 2-(4-hydroxyphenylthio)-7-isopropoxy-5-methoxychromone.

6. An aldose reductase inhibitor composition comprising as an active ingredient a chromone derivative of formula (1):

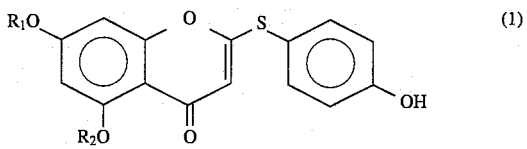

wherein $R_1$ and $R_2$ are the same or different and independently represent a hydrogen atom or a lower alkyl group and a pharmaceutically acceptable carrier.

7. The aldose reductase inhibitor according to claim 6, wherein in formula (1) at least one of $R_1$ and $R_2$ is a branched-chain alkyl group represented by formula (3):

wherein $R_7$ and $R_8$ are the same or different and independently represent methyl or ethyl group.

8. The aldose reductase inhibitor according to claim 6, wherein in formula (1) at least one of $R_1$ and $R_2$ is an isopropyl group.

9. An aldose reductase inhibitor composition comprising as an active ingredient 5,7-dihydroxy-2-(4-hydroxyphenylthio)chromone, 5-hydroxy-2-(4-hydroxyphenylthio)-7-methoxychromone, 2-(4-hydroxyphenylthio)-5,7-dimethoxychromone, 5,7-diethoxy-2-(4-hydroxyphenylthio)chromone, 5-hydroxy-2-(4-hydroxyphenylthio)-7-isopropoxychromone, 2-(4-hydroxyphenylthio)-7-isopropoxy-5-methoxychromone, 5-ethoxy-2-(4-hydroxyphenylthio)-7-isopropoxychromone, 2-(4-hydroxyphenylthio)-5,7-diisopropoxychromone, 2-(4-hydroxyphenylthio)-5,7-dipropoxychromone, 5,7-dibutoxy-2-(4-hydroxyphenylthio)chromone, 5,7-di-s-butoxy-2-(4-hydroxyphenylthio)chromone, 7-s-butoxy-2-(4-hydroxyphenylthio)-5-isopropoxychromone, 7-s-butoxy-5-ethoxy-2-(4-hydroxyphenylthio)chromone, 7-s-butoxy-2-(4-hydroxyphenylthio)-5-methoxychromone or 7-(1-ethylpropoxy)-2-(4-hydroxyphenylthio)-5-methoxychromone and a pharmaceutically acceptable carrier.

10. The aldose reductase inhibitor of claim 9, wherein said active ingredient is 2-(4-hydroxyphenylthio)-7-isopropoxy-5-methoxychromone.

* * * * *